United States Patent [19]

McCombs

[11] Patent Number: 5,041,613
[45] Date of Patent: Aug. 20, 1991

[54] ORGANIC COMPOSITIONS AND THEIR MANUFACTURE

[75] Inventor: Charles A. McCombs, Kingsport, Tenn.

[73] Assignee: Eastman Kodak Company, Rochester, N.Y.

[21] Appl. No.: 399,790

[22] Filed: Aug. 28, 1989

[51] Int. Cl.$^5$ .............................................. C07C 69/74
[52] U.S. Cl. .................................. 560/126; 544/335; 544/336; 546/341; 546/342; 548/146; 548/237; 549/78; 549/79; 549/454; 560/51; 560/53; 560/118; 560/231; 568/42; 568/314; 568/346
[58] Field of Search ............... 560/126, 51, 53, 118, 560/231; 568/346, 42, 314; 544/335, 336; 546/341, 342; 548/146, 237; 549/78, 79, 454

[56] References Cited

U.S. PATENT DOCUMENTS 3,997,590 12/1976 Lester .................................. 260/470

FOREIGN PATENT DOCUMENTS 2090246 7/1982 United Kingdom .

Primary Examiner—Michael L. Shippen
Attorney, Agent, or Firm—Bernard J. Graves, Jr.; S. E. Reiter; William P. Heath, Jr.

[57] ABSTRACT

Processes, intermediates, and products involved in preparing cyclohexanediones of the formula

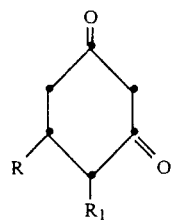

are disclosed. An aldehyde of the formula R—CHO is reacted with a ketone type compound of the formula $(R_1)(R_2)C=C=O$ at a temperature below about 110° C. to give a polymer having the repeating unit $—OCH(R)C(R_1)(R_2)CO]_n$ wherein n ranges from about 2 to about 1,000. The polymer is hydrolyzed with alcoholic or aqueous base to produce a mixture of an unsaturated acid of the formula $R—CH=C(R_1)—COOH$ and a hydroxy ester or acid of the formula $R—CH(OH)C(R_1)(R_2)—COOR_3$, the mixture is then contacted with an esterifying agent to convert the acids to esters. The ester mixture is contacted with a dehydrating agent to convert the hydroxy ester to unsaturated ester of the formula $R—CH=C(R_1)—COOR_3$. The unsaturated ester is contacted with a basic catalyst to cyclize it to the cyclic dione ester of the formula

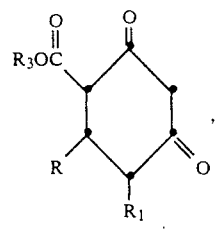

and this ester is then hydrolyzed and decarboxylated to give the product

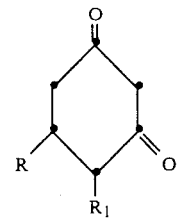

wherein:
R is selected, e.g., from alkylthio, alkythioalkyl, cycloalkyl, alkyl substituted cycloalkyl, alkoxy, alkanoyloxy, alkoxycarbonyl, aryl, substituted aryl, heterocyclic, or substituted heterocyclic, wherein each group or moiety has up to 20 carbons; and
$R_1$, $R_2$ and $R_3$ are each selected, e.g., from alkyl or cycloalkyl of up to 20 carbons, and $R_2$ and $R_3$ can also be hydrogen.

4 Claims, No Drawings

ORGANIC COMPOSITIONS AND THEIR MANUFACTURE

This invention relates to novel compositions of matter and their preparation, which compositions are useful in the preparation of a wide variety of useful organic materials, e.g., in the manufacture of herbicidal compositions.

BACKGROUND

The compound:

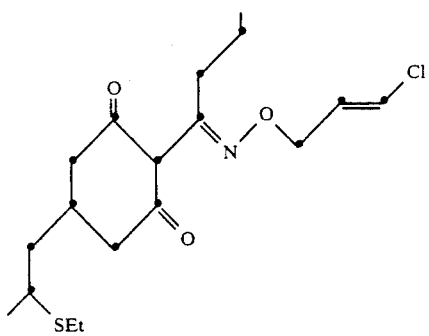

is known to have herbicidal activity. This herbicidal compound can be prepared from the dione:

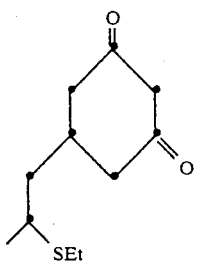

which has been prepared by condensation of acetoacetic acid and 3-ethylthio-butyraldehyde, followed by Michael addition with diethyl malonate, hydrolysis, and decarboxylation. Simplified synthetic routes to the above-described dione would be desirable, so that fewer reaction steps would be required, the use of expensive reagents (such as diethyl malonate) could be avoided, and other similar compounds could be readily prepared.

STATEMENT OF THE INVENTION

In accordance with the present invention, there are provided several novel compositions which are useful, for example, as chemical intermediates for the preparation of herbicides. The invention compositions include:

(a) polyester material having the repeating unit of the formula

wherein n ranges from about 2 up to 1,000;

(b) acids and esters of the formula R—CH=C(R$_1$)—COOR$_3$ (cis and trans configuration);

(c) acids and esters of the formula R—CH(OH)C(R$_1$)(R$_2$)COOR$_3$;

(d) esters of the formula

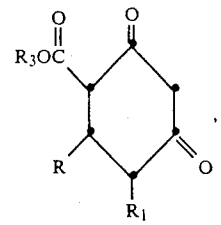

and (e) compounds of the formula

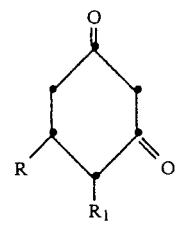

The processes for preparing these compositions are unique and are described in detail below.

The herbicidal manufacturing utility of the invention compositions is demonstrated for example, in the application of the present invention to the preparation of certain 1,3-cyclohexanediones of the general formula

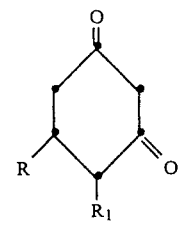

wherein R and R$_1$ are defined below, which diones are intermediates in the preparation of such herbicides as are disclosed in U.K. Patent 2,090,246, the disclosure of which is incorporated herein by reference.

DETAILED DESCRIPTION OF THE INVENTION

In accordance with the present invention, there are provided novel compositions of matter comprising polyester material having the repeating unit of the formula

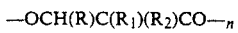

n ranges from about 2 to about 1,000;

R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein the alkyl groups or moieties have 1 to 20 carbons; and R$_1$ and R$_2$ are each selected from hydrogen, alkyl of 1 to 20 carbons, or cycloalkyl.

In accordance with a particular embodiment of the present invention, there is provided a process for preparing the above-described polyester material comprising reacting an aldehyde of the formula R—CHO with a ketene type compound of the formula (R$_1$)(R$_2$)—C=C=O at a temperature below about 110° C.

In accordance with another embodiment of the present invention, there is provided a composition of matter of the formula

R—CH=C(R$_1$)—COOR$_3$ wherein:

R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein the alkyl groups or moieties have 1 to 20 carbons; and R$_1$ and R$_3$ are each selected from hydrogen, alkyl of 1 to 20 carbons, or cycloalkyl.

In accordance with yet another embodiment of the present invention, there is provided a process for preparing the above-described composition comprising contacting the above-described polyester material with alcoholic or aqueous base, optionally followed by contacting with C$_1$-C$_6$ alcohol.

In accordance with still another embodiment of the present invention, there is provided a composition of matter of the formula

R—CH(OH)CH(R$_1$)—COOR$_3$ wherein:

R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein the alkyl groups or moieties have 1 to 20 carbons; and R$_3$ is hydrogen, alkyl of 1 to 20 carbons, or cycloalkyl.

In accordance with a further embodiment of the present invention, there is provided a process for preparing the above-described composition comprising contacting the above-described polyester material with aqueous or alcoholic base.

In accordance with a still further embodiment of the present invention, there is provided a process for preparing a compound of the formula

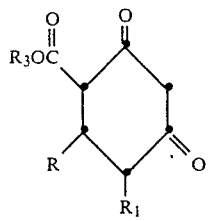

comprising reacting an ester of the formula:

R—CH=C(R$_1$)—COOR$_3$ with an ester of the formula R$_3$OOCCH$_2$COCH$_3$ in the presence of a basic catalyst, wherein:

R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein the alkyl groups or moieties have 1 to 20 carbons;

R$_1$ is hydrogen, alkyl off 1 to 20 carbons, or cycloalkyl; and

R$_3$ is alkyl of 1 to 20 carbons or cycloalkyl.

In accordance with another embodiment of the present invention, there is provided process for preparing cyclohexanediones of the formula

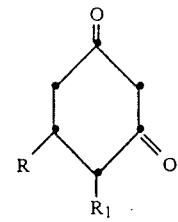

comprising:

(i) reacting an aldehyde of the formula R—CHO with a ketene type compound of the formula (R$_1$)(R$_2$)C=C=O at a temperature below about 110° C. to give a polymer having the repeating unit +OCH(R)C(R$_1$)(R$_2$)CO+$_n$ wherein n ranges from about 2 to about 1,000, (ii) contacting said polymer with alcoholic base to hydrolyze the same to a mixture of an unsaturated acid of the formula R—CH=C(R$_1$)—COOH and a hydroxy ester of the formula R—CH(OH)C(R$_1$)(R$_2$)—COOR$_3$, (iii) contacting said mixture with an esterifying agent to convert the unsaturated acid to ester of the formula R—CH=C(R$_1$)—COOR$_3$, (iv) contacting the ester mixture with a dehydrating agent to convert said hydroxy ester to said unsaturated ester of the formula R—CH=C(R$_1$)—COOR$_3$, (v) contacting said unsaturated ester with a basic catalyst to cyclize the unsaturated ester to the cyclic dione ester of the formula

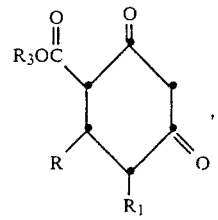, and (vi) hydrolyzing and decarboxylating said cyclic dione ester to give the product

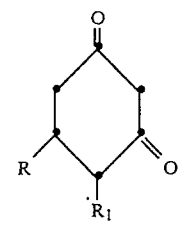

wherein:

R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein the alkyl groups or moieties have 1 to 20 carbon; and R$_1$, R$_2$ and R$_3$ are each selected from hydrogen or alkyl of 1 to 20 carbons, or cycloalkyl.

In accordance with yet another embodiment of the present invention, there is provided process for preparing cyclohexanediones of the formula

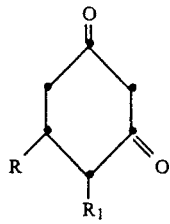

comprising reacting an aldehyde of the formula R—CHO with a ketene type compound of the formula $(R_1)(R_2)C\!=\!C\!=\!O$ at a temperature below about 110° C. to give a polymer having the repeating unit

—OCH(R)C(R$_1$)(R$_2$)CO—$_n$ wherein n ranges from about 2 to about 1,000, contacting said polymer with aqueous base to hydrolyze the same to a mixture of an unsaturated acid of the formula $(R\!-\!CH\!=\!C(R_1))\!-\!COOH$ and a hydroxy acid of the formula $R\!-\!CH(OH)C(R_1)(R_2)\!-\!COOH$, contacting said mixture with an esterifying agent to convert the unsaturated acid to ester of the formula $R\!-\!CH\!=\!C(R_1)\!-\!COOR_3$, and the hydroxy acid to ester of the formula $R\!-\!CH(OH)C(R_1)(R_2)\!-\!COOR_3$, contacting the ester mixture with a dehydrating agent to convert the hydroxy ester to said unsaturated ester, contacting said unsaturated ester with a basic catalyst to cyclize the unsaturated ester to the cyclic dione ester of the formula

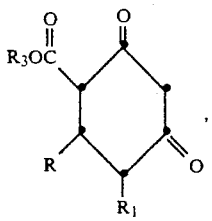

and hydrolyzing and decarboxylating said cyclic dione ester to give the product

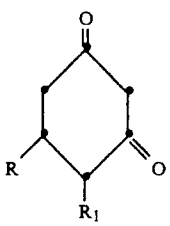

wherein:
R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein the alkyl groups or moieties have 1 to 20 carbons; and $R_1$, $R_2$ and $R_3$ are each selected from hydrogen or alkyl of 1 to 20 carbons, or cycloalkyl.

In accordance with yet another embodiment of the present invention, there is provided composition of matter comprising a compound of the formula

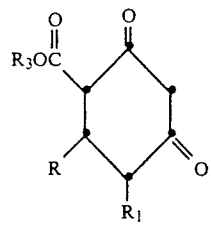

wherein:
R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein the alkyl groups or moieties have 1 to 20 carbons; and $R_1$ and $R_3$ are each selected from hydrogen or alkyl of 1 to 20 carbons, or cycloalkyl.

In accordance with yet another embodiment of the present invention, there is provided composition of matter comprising a compound of the formula

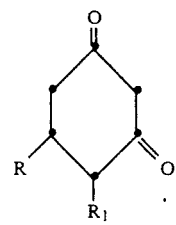

wherein:
R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein the alkyl groups or moieties have 1 to 20 carbons; and $R_1$ is alkyl of 1 to 20 carbons, or cycloalkyl.

In one aspect, the invention comprises contacting an aldehyde reactant of the formula R—CHO with a ketene reactant of the formula $(R_1)(R_2)C\!=\!C\!=\!O$ at a temperature below about 110° C., to give a polyester having the repeating unit

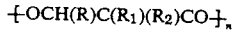

$+\!OCH(R)C(R_1)(R_2)CO\!+_n$ wherein n ranges from about 2 to about 1,000.

This polyester material can be further converted by treating said polyester at a temperature of from about 0° C. to about 100° C. with aqueous or alcoholic base to hydrolyze the polyester. This produces a mixture of the unsaturated acid, $R\!-\!CH\!=\!C(R_1)\!-\!COOH$, and from none to minor amounts of the hydroxy acid when aqueous base is employed; while when alcoholic base is employed, the ester of the hydroxy acid is obtained.

This reaction mixture containing unsaturated acid, hydroxy acid and/or ester of the hydroxy acid can be further converted by treating said product mixture with an esterification agent, followed by a dehydrating agent to convert essentially all product to the unsaturated ester of the formula $R\!-\!CH\!=\!C(R_1)\!-\!COOR_3$. The above-identified unsaturated ester can then be further converted by reacting said unsaturated ester in ethanolic sodium ethoxide with an acetoacetate ester of the formula $CH_3COCH_2COOR_3$ to give the cyclic ester

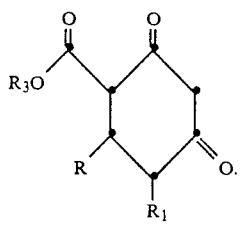

The above cyclic ester can be further converted by hydrolyzing and decarboxylating to remove the

group, to give a 1,3-cyclohexanedione of formula (VI).

Examples of $R_1$, $R_2$ and $R_3$ substituents are hydrogen, $-CH_3$, $-C_2H_5$, $-C_3H_7$, $-C_4H_9$, $-C_5H_{11}$, and $-C_6H_{13}$.

Examples of R substituents are cyclohexyl,

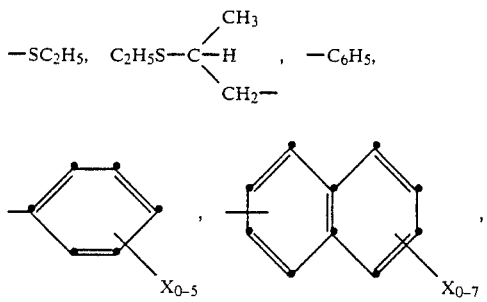

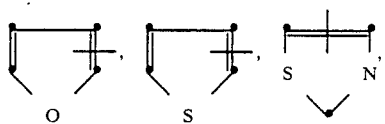

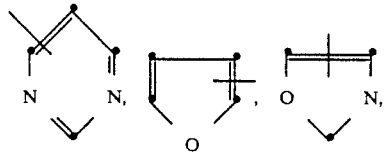

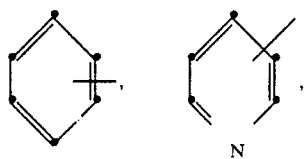

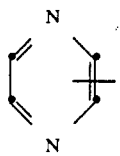

or any of the above heterocyclic structures wherein two adjacent hydrogens are replaced with

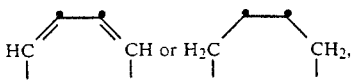

and wherein each X substituent, when present, is in any available ring position and is selected independently from alkyl of 1 to 6 carbons, alkoxy of 1 to 6 carbons, or halogen.

The novel polymers of the present invention are prepared as follows:

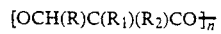

In this process, it is desirable to employ a Lewis acid catalyst, with the various organic zinc salts of the formula $Zn(OR')_2$ wherein R' is alkanoyl, straight or branched chain, of 2 to 20 carbons being preferred. Presently, most preferred are organic zinc salts of the above formula wherein R, has 5 to 10 carbons, e.g., 2-ethylhexanoyl.

The molar concentration of the catalyst with respect to the aldehyde reactant can vary widely, e.g., from about 0.2% to about 10.0%, preferably from about 0.5% to about 3.0%, and most preferably from about 1.0% to about 2.5%.

The reaction temperature is preferably below about 110° C., although higher temperatures may be employed if provision is made to prevent reactant degradation or excessive side reactions.

In this procedure, the solvent is selected from essentially any organic solvent which does not react under the reaction conditions, and includes such solvents as benzene, kerosene, or the like. The ratio of solvent in (mL) to aldehyde reactant in (g.mole) can be, e.g., from about 20/1 to about 1,000/1, preferably from about 80/1 to about 500/1, and most preferably from about 110/1 to about 200/1.

The novel polyesters of the present invention can be converted by subjecting polymer to alcoholic base hydrolysis, with novel compositions obtained therefrom as follows:

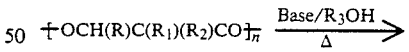

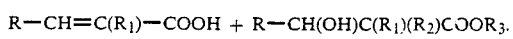

Bases useful for this conversion include the metal hydroxides, alkoxides and the like. Preferably the base is sodium hydroxide or sodium methoxide. Suitable reaction temperatures fall in the range of about 20° C. to reflux. Reaction times typically fall in the range of about 1-5 hours. The molar ratio of base to polymer typically falls in the range of about 1/5 to about 5/1, with about 1/1 being most preferred. The weight ratio of polymer to alcohol typically falls in the range of about 1/1 to about 1/50, with from about 1/10 to about 1/30 being most preferred.

The novel polyesters of the present invention can also be converted by subjecting polymer to hydrolysis with aqueous base, with novel compositions obtained therefrom as follows:

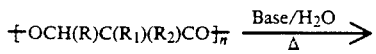

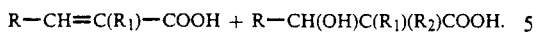

The reaction parameters given above for the alcoholic base hydrolysis also apply to this aqueous hydrolysis with the weight ratio of polymer to water being as with the alcohol.

The unsaturated acides prepared as described above can be further converted in the presence of alcohol and acid, with novel compositions obtained therefrom as follows:

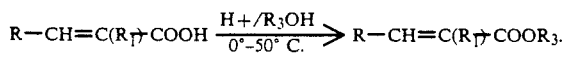

Typical useful acid catalysts include thionyl chloride and protonic acids, organic or inorganic. Preferably the proton donor is derived from thionyl chloride, sulfuric acid or hydrochloric acid. The reaction temperature typically employed falls between about 20° C. and about 35° C. The reaction period typically employed falls in the range of about 0.5 to about 2.5 hours. The molar ratio of proton donor (e.g., SOCl$_2$) to alcohol (e.g., MeOH) typically employed falls in the range of about 1/5 to about 1/100, and the molar ratio of alcohol to unsaturated acid typically employed falls in the range of about 10/1 to about 500/1.

The hydroxy acids prepared as described above can be further converted in the presence of alcohol and acid, with novel reaction scheme and novel compositions obtained therefrom as follows:

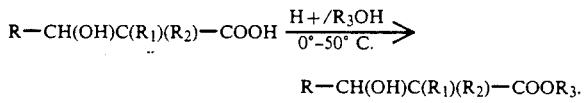

The reaction parameters given above for the esterification of the unsaturated acid also apply to this esterification reaction.

The hydroxyesters prepared as described above can be further converted by contacting with a dehydrating agent, with novel compositions obtained therefrom as follows:

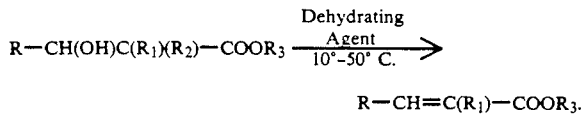

Typical useful dehydrating or protonating agents include toluene sulfonyl chloride (TsCl), H$_2$SO$_4$, H$_3$PO$_4$, and p-toluenesulfonic acid. The molar ratios of the hydroxy ester/dehydrating agent can vary widely, e.g., from about 1/1 to about 1/20, with from about 1/5 to about 1/10 being preferred. Pyridine is the preferred solvent when this conversion is carried out with TsCl as the dehydrating or protonating agent. Solvent is typically employed in a weight ratio of solvent/hydroxy ester in the range of about 15/1 to about 1/1, preferably from about 10/1 to about 2/1. The preferred reaction temperature is from about 18° C to about 25° C.

The unsaturated esters prepared as described above can be further converted by contacting with acetoacetate moieties, with compositions obtained therefrom as follows:

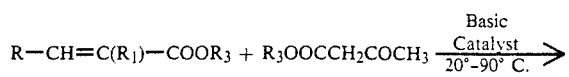

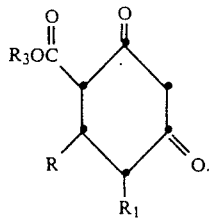

The useful basic catalysts include the Groups IA and IIA metal alkoxides of C$_1$-C$_6$ aliphatic alcohols, or the hydroxides of these metals. The preferred molar ratio of basic catalyst to total moles of reactants is from about 0.10 to about 10.0, most preferably from about 1 to about 4. The molar ratio of acetoacetic ester to unsaturated ester is from about 0.8 to about 1.5, preferably from about 1.0 to about 1.1. The weight ratio of total reactants to the alcohol (preferably 1–6 carbons) is from about 0.01 to about 1.2, preferably from about 0.08 to about 1.0. The reaction temperature is from about 20° to about 90° C., preferably from about 70° to about 78° C. The reaction time is preferably from about 10 to about 24 hours.

The following nonlimiting examples will further illustrate the invention.

EXAMPLE 1

Poly(5-Ethylthio-3-Hydroxyhexanoate) (PEH)

3-Ethylthiobutyraldehyde (25.08 g, 0.189 mole) and 2.0 mL of a 1.4M solution of zinc 2-ethylhexanoate were dissolved in 30 mL of toluene and cooled in a water bath. Ketene was distilled into this solution through a submerged inlet at such a rate to maintain the temperature below about 50° C. When exotherm subsided after about 30 to about 40 minutes, the ketene purge was discontinued and the solution was stirred for 1 hour. Toluene was evaporated to give 38.0 g of crude polyester which was used without further purification. Analysis of this polyester gave:

IR (thin film) 1740 cm$^{-1}$;

NMR (CDCl$_3$) ppm 5.4 (m, 1H); 3.2–2.2 (m, 5H); 2.2–1.6 (m, 2H), 1.32 (d, 3H); 1.25 (t, 3H).

The n value for this sample is believed to range between about 2 and 200.

EXAMPLE 2

5-Ethylthio-2-Hexenoic Acid (EHA)

The polyester of Example 1 (0.5 g, 2.9 mmole based on nw of 174 of the repeating unit) and sodium methoxide (0.16 g, 2.9 mmole) were admixed with 10 mL of methanol and heated to reflux for 2.5 hours. After cooling, the methanol solution was evaporated, and the residue was partitioned between toluene and aqueous acid (e.g., 1.0N HCl). The toluene extract was dried over sodium sulfate and evaporated to give 0.37 g of a dark-colored oil product which contained about 0.25 g of EHA and minor amounts of the hydroxy methyl ester (HME). Analysis of the oil product gave:

IR (thin film) 3500*, 1710 cm$^{-1}$;

NMR (CDCl₃) ppm; *7.6 (m, OH); 7.4–5.5 (m, olefin CH); *4.3 (M, CHOH); 4.2 (bs, COOMe); 3.5–0.7 (nondescript multiplet with ethylthiopeaks protruding from multiplet)

The asterisk noted data show the presence of HME which typically would be produced in amounts comprising less than about 40 mole % based on total moles of EHA and HME produced.

EXAMPLE 3

The polyester (1.0 g) of Example 1 and sodium hydroxide (0.32 g) were admixed with 20 mL methanol, and heated to reflux for 2.5 hours. Methanol was evaporated and the residue partitioned between aqueous acid and methylene chloride. The organic layer was removed, dried over sodium sulfate, and then evaporated to afford 0.94 g of red oil as in Example 2 containing both EHA and HME. This red oil (0.94 g) dissolved in 5 mL of methanol was mixed with 1 mL of thionyl chloride and the mixture heated gently for a few minutes, and the solution was then allowed to stand for about 75 minutes. Methanol was evaporated and the residue distilled to afford 0.61 g (56%) of unsaturated ester (MEH) and a minor amount of the hydroxy methyl ester.

EXAMPLE 4

Methyl 5-Ethylthio-2-Hexenoate (MEH)

The polyester of Example 1 (38 g crude) and sodium methoxide (11.3 g, 0.209 mole) were added to 100 mL of methanol, and the solution was heated to reflux for 3 hours. The methanol solution was cooled and placed in an ice bath. To this cooled solution was added thionyl chloride (22.8 g, 0.191 mole) dropwise slowly over 30 minutes and was allowed to stand overnight. The methanol was evaporated, and the residue was partitioned between methylene chloride (CH₂Cl₂) and aqueous sodium bicarbonate. The CH₂Cl₂ layer was dried over sodium sulfate and distilled to afford 21.0 g (58.8%) of MEH as a yellow oil having a bp of 75° to 90° C. at 2.5 to 3.0 mm Hg. The distillate still contained some of the HME.

IR (thin film) 1720 cm⁻¹.

NMR (CDCl₃) ppm 7.05 (d of t, 1H, J=7, 16 Hz); 5.88 (bd, 1H, J=16 Hz); 3.82 (5, 3H); 3.3–1.1 (nondescript multiplet) 1.30 (d, 3H, J=6 Hz); 1.20 (t, 3H, J=6 Hz).

Part of the distillate (16.0 g) was dissolved in 25 mL of pyridine (pyd), to which 28.3 g of toluene sulfonyl chloride (TsCl) was added. The solution was heated for 2 hours at about 60° C, then cooled and the pyridine evaporated. The residue was dissolved in aqueous acid and methylene chloride. The organic layer was isolated, dried over sodium sulfate and then distilled to remove solvent and afford 11.2 g of MEH. The presence of HME was not detected.

EXAMPLE 5

Preparation of 4-Carboethoxy-5-[2-(ethylthio)-propyl]-1,3-cyclohexanedione

The unsaturated ester of the formula CH₃CH₂S(CH₃)CHCH₂CH=CHCOOCH₃ (1.0 g, 5.3 mmole) is added to a solution of ethyl acetoacetate (0.68 g, 5.3 mmole) and sodium metal (0.36 g, 16.9 mmole) in 20 mL of dry ethanol and heated to reflux for 18 hours. After cooling, the ethanol is evaporated and partitioned between H₂O and CH₂Cl₂. The aqueous product layer is acidified with HCl to pH=1 and extracted with CH₂Cl₂. This organic layer is dried over sodium sulfate and evaporated to give 0.88 g (57.8%) of product as a yellow oil which is partially crystalline. The target product is identified by IR and NMR. By known hydrolysis and decarboxylation procedures this product is convertible to 5-[2-(ethylthio)-propyl]-1,3-cyclohexanedione.

The invention now being fully described, it will be apparent to one of ordinary skill in the art that many changes and modifications can be made thereto without departing from the spirit or scope of the invention as set forth herein.

I claim:

1. The process for preparing a compound of the formula

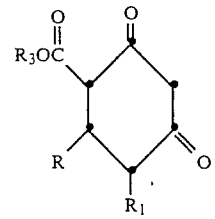

comprising (i) reacting an aldehyde of the formula R—CHO with a ketene type compound of the formula $(R_1)(R_2)C=C=O$ at a temperature below about 100° C. to give a polymer having the repeating unit $+OCH(R)C(R_1)(R_2)CO+_n$ wherein n ranges from about 2 to about 1,000, (ii) contacting said polymer with alcoholic base to hydrolize the same to a mixture of an unsaturated acide of the formula R—CH=C(R₁)—COOH and a hydroxy ester of the formula R—CH(OH)C(R₁)(R₂)COOR₃, (iii) containing said mixture with an esterifying agent to convet the unsaturated acid to ester of the formula R—CH=C(R₁)—COOR₃, (iv) contacting the ester mixture with a dehydrating agent to convert said hydroxy ester to said unsaturated ester of the formula R—CH=C(R₁)—COOR₃, (v) contacting said unsaturated ester in the presence of a compound of the formula R₃OOCCH₂COCH₃ with a basic catalyst to cyclize the unsaturated ester to the cyclic dione ester of the formula

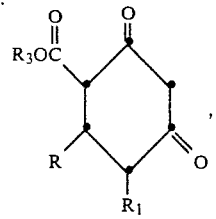

wherein:

R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein each group or moiety has up to 20 carbons:

$R_1$ is hydrogen, alkyl or cycloalkyl of up to 20 carbons;

$R_2$ is hydrogen; and $R_3$ *is alkyl or cycloalkyl of up to* 20 carbons.

2. The process of claim 1 wherein $R_3$ is $-CH_3$ or $-CH_2CH_3$; $R_1$ is H; and R is $CH_3CH_2S(CH_3)CHCH_2-$.

3. The process for preparing cyclo-hexanediones of the formula

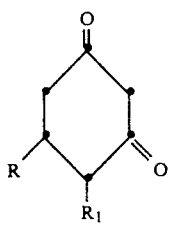

comprising:
(i) reacting an aldehyde of the formula R—CHO with a ketene type compound of the formula $(R_1)(R_2)C=C=O$ at a temperature below about 110° C. to give a polymer having the repeating unit $-[OCH(R)C(R_1)(R_2)CO]_n$ wherein n ranges from about 2 to about 1,000,
(ii) contacting said polymer with alcoholic base to hydrolyze the same to a mixture of an unsaturated acide of the formula $R-CH=C(R_1)=COOH$ and a hydroxy ester of the formula $R-CH(OH)C(R_1)(R_2)COOR_3$,
(iii) contacting said mixture with an esterifying agent to convert the unsaturated acid to ester of the formula $R-CH=C(R_1)=COOH_3$,
(iv) contacting the ester mixture with a dehydrating agent to convert said hydroxy ester to said unsaturated ester of the formula $R-CH=C(R_1)=COOH_3$,
(v) contacting said unsaturated ester in the presence of a compound of the formula $R_3OOCCH_2COCH_3$ with a basic catalyst to cyclize the unsaturated ester to the cyclic dione ester of the formula

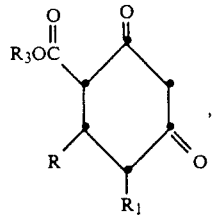

(vi) hydrolyzing and decarboxylating said cyclic dione ester to give the product

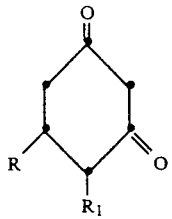

wherein:
R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein each group or moiety has up to 20 carbons; and $R_1$ and $R_3$ are each selected from hydrogen or alkyl or cycloalkyl of up to 20 carbons; and $R_2$ is hydrogen.

4. The process for preparing cyclohexanediones of the formula

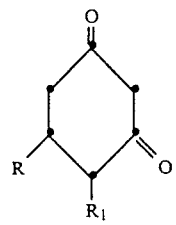

comprising reacting an aldehyde of the formula R—CHO with a ketene type compound of the formula $(R_1)(R_2)C=C=O$ at a temperature below about 110° C. to give a polymer having the repeating unit $-OCH(R)C(R_1)(R_2)CO]_n$ wherein n ranges from about 2 to about 1,000, contacting said polymer with aqueous base to hydrolyze the same to a mixture of an unsaturated acid of the formula $R-CH=C(R_1)-COOH$ and a hydroxy acid of the formula $R-CH(OH)C(R_1)(R_2)-COOH$, contacting said mixture with an esterifying agent to convert the unsaturated acide to ester of the formula $R-CH=C(R_1)-COOR_3$, and the hydroxy acid to ester of the formula $R-CH(OH)C(R_1)(R_2)-COOR_3$ contacting the ester mixture with a dehydrating agent to convert the hydroxy ester to said unsaturated ester, contacting said unsaturated ester with a basic catalyst to cyclize the unsaturated ester to the cyclic dione ester of the formula

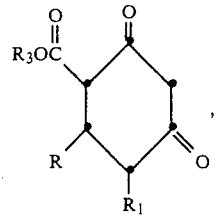

and hydrolyzing and decarboxylating said cyclic dione ester to give the product

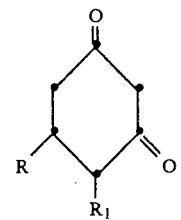

wherein:
R is selected from alkylthio, alkylthioalkyl, cycloalkyl, alkyl substituted cycloalkyl, alkoxy, alkanoyloxy, alkoxycarbonyl, aryl, substituted aryl, heterocyclic, or substituted heterocyclic, wherein each group or moety has up to 20 carbons; and $R_1$ and $R_3$ are each selected from hydrogen or alkyl or cycloalkyl of up to 20 carbons; and $R_2$ is hydrogen.

* * * * *

UNITED STATES PATENT AND TRADEMARK OFFICE
CERTIFICATE OF CORRECTION

PATENT NO. : 5,041,613

DATED : August 20, 1991

INVENTOR(S) : Charles A. McCombs

Page 1 of 2

It is certified that error appears in the above-identified patent and that said Letters Patent is hereby corrected as shown below:

Claim 1, column 12, line 36, "hydrolize" should be ---hydrolyze---.

line 37, "acide" should be ---acid---.

line 40, "containing" should be ---contacting---.

Claim 3, column 13, line 8, "cyclo-hexanediones" should be ---cyclohexanediones".

line 28, "acide" should be ---acid---.

line 28, "R-CH=C($R_1$)=COOH" should be ---R-CH=C($R_1$)-COOH---.

line 33, "R-CH=C($R_1$)=COOH$_3$" should be ---R-CH=C($R_1$)-COOR$_3$---.

lines 36 and 37, "R-CH=C($R_1$)=COOH$_3$" should be ---R-CH=C($R_1$)-COOR$_3$---.

line 47, after the formula, insert ---and---.

UNITED STATES PATENT AND TRADEMARK OFFICE
CERTIFICATE OF CORRECTION

PATENT NO. : 5,041,613

DATED : August 20, 1991

INVENTOR(S) : Charles A. McCombs

It is certified that error appears in the above-identified patent and that said Letters Patent is hereby corrected as shown below:

Claim 4, column 14, line 23, "$-OCH(R)C(R_1)(R_2)CO]_n$" should be --- $\{OCH(R)C(R_1)(R_2)CO\}_n$ ---.

line 29, "acide" should be ---acid---.

line 65, "moety" should be ---moiety---.

Signed and Sealed this

Ninth Day of March, 1993

Attest:

STEPHEN G. KUNIN

Attesting Officer

Acting Commissioner of Patents and Trademarks